US011412975B2

(12) United States Patent
Liu et al.

(10) Patent No.: US 11,412,975 B2
(45) Date of Patent: Aug. 16, 2022

(54) SYSTEM AND METHOD FOR MEASURING FUNCTIONAL BRAIN SPECIALIZATION

(71) Applicants: Hesheng Liu, Marblehead, MA (US); Danhong Wang, Belmont, MA (US); Randy L. Buckner, Newton, MA (US)

(72) Inventors: Hesheng Liu, Marblehead, MA (US); Danhong Wang, Belmont, MA (US); Randy L. Buckner, Newton, MA (US)

(73) Assignee: The General Hospital Corporation, Boston, MA (US)

(*) Notice: Subject to any disclaimer, the term of this patent is extended or adjusted under 35 U.S.C. 154(b) by 1732 days.

(21) Appl. No.: 14/672,046

(22) Filed: Mar. 27, 2015

(65) Prior Publication Data
US 2015/0272493 A1 Oct. 1, 2015

Related U.S. Application Data

(60) Provisional application No. 61/972,004, filed on Mar. 28, 2014.

(51) Int. Cl.
A61B 5/00 (2006.01)
A61B 5/055 (2006.01)

(52) U.S. Cl.
CPC .......... A61B 5/4064 (2013.01); A61B 5/0042 (2013.01); A61B 5/055 (2013.01); A61B 5/742 (2013.01)

(58) Field of Classification Search
CPC ..... A61B 5/4064; A61B 5/0042; A61B 5/055; A61B 5/742; G01R 33/48006; G06T 2207/20156

(Continued)

(56) References Cited

U.S. PATENT DOCUMENTS

2011/0077503 A1* 3/2011 Bonilha ................ A61B 5/055 600/411
2013/0102877 A1* 4/2013 Mori ...................... A61B 5/055 600/410

(Continued)

OTHER PUBLICATIONS

Beckmann et al. "Investigations into resting state connectivity using independent component analysis". Phil. Trans. R. Soc., 2005. 360, p. 1001-1013. (Year: 2005).*

(Continued)

Primary Examiner — Catherine B Kuhlman
Assistant Examiner — Sean A Frith
(74) Attorney, Agent, or Firm — Quarles & Brady LLP

(57) ABSTRACT

A system and method for measuring a functional lateralization of a subject brain is provided. The method includes providing a set of functional magnetic resonance imaging (fMRI) data acquired during a resting state of a subject, and selecting a plurality of seed voxels associated with locations in hemispheres of a brain of the subject. The method also includes determining a degree of within-hemisphere connectivity for each seed voxel using the fMRI data, determining a degree of cross-hemisphere connectivity for each seed voxel using the fMRI data, and computing an autonomy index for each seed voxel using the degree of within-hemisphere connectivity and the degree of cross-hemisphere connectivity, wherein the autonomy index is indicative of a connectivity asymmetry between the hemispheres. The method further includes generating a report indicative of a specialization profile determined for a region of interest in the brain of the subject.

10 Claims, 8 Drawing Sheets

(58) Field of Classification Search
USPC .......................................................... 600/410
See application file for complete search history.

(56) References Cited

U.S. PATENT DOCUMENTS

2013/0113816 A1* 5/2013 Sudarsky .............. G06T 11/206
345/589
2014/0371573 A1* 12/2014 Komoto ............. A61B 5/04842
600/411

OTHER PUBLICATIONS

Margulies et al. "Mapping the functional connectivity of anterior cingulate cortex". NeuroImage, 2007. vol. 37, p. 579-588. (Year: 2007).*
Razlighi, Q., et al., "Resting State Inter and Intra Hemispheric Human Brain Functional Connectivity", Conf Prof IEEE Eng Med Biol Soc, 2013: 6522-6525 (Year: 2013).*
Gotts, S., et al. "Two Distinct forms of functional lateralization in the human brain", PNAS, 2013. p. E3435-E3444 (Year: 2013).*
Saad, Z., et al. "Correcting Brain-wide correlation differences in resting-state fMRI," Brain Connectivity. vol. 3(4). 2013. p. 339-352. (Year: 2013).*
Jo, H., et al. "Quantifying Agreement between Anatomical and Functional Interhemispheric Correspondences in the Resting Brain", Plos One, 7(11), 2012. p. 1-11. (Year: 2012).*

* cited by examiner

Discovery (N=500)

Replication (N=500)

-0.02   0.02   0.06

FIG. 5A
FIG. 5B
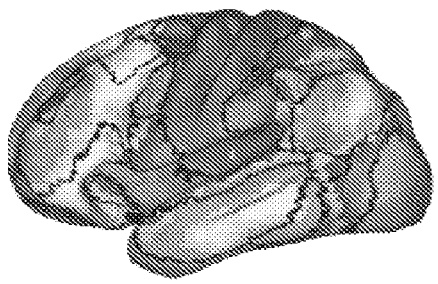
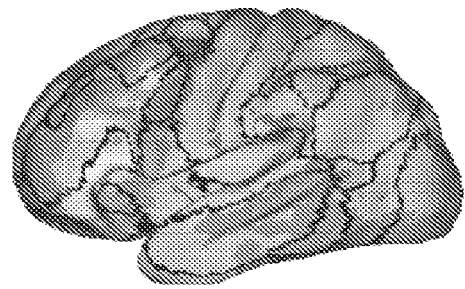
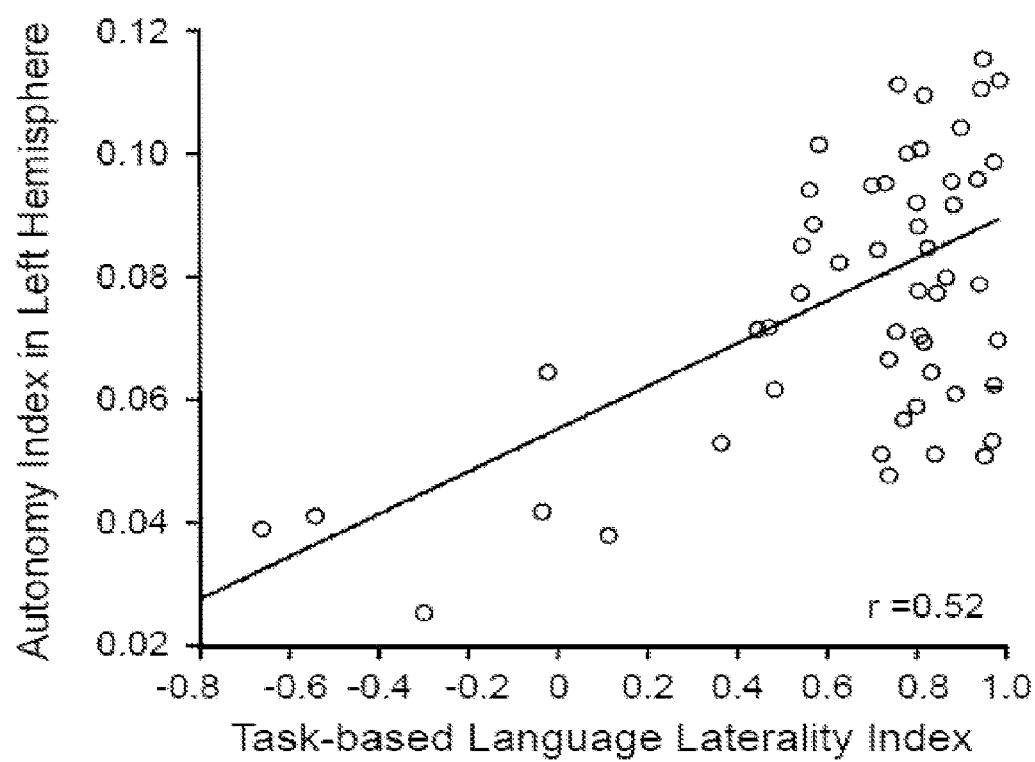
FIG. 5C

SYSTEM AND METHOD FOR MEASURING FUNCTIONAL BRAIN SPECIALIZATION

CROSS-REFERENCE TO RELATED APPLICATIONS

This application claims the benefit of U.S. Provisional Patent Application Ser. No. 61/972,004, filed on Mar. 28, 2014, and entitled "SYSTEM AND METHOD FOR MEASURING FUNCTIONAL BRAIN SPECIALIZATION."

STATEMENT REGARDING FEDERALLY SPONSORED RESEARCH

This invention was made with government support under K25NS069805 awarded by the National Institutes of Health. The government has certain rights in the invention.

BACKGROUND

The present disclosure relates generally to systems and methods for functional magnetic resonance imaging and, in particular, to systems and methods for estimating functional brain specialization.

A fundamental property of brain organization is the presence of structural and functional asymmetries between hemispheres. Lateralization of function is thought to contributed to the evolution of human language and reasoning by providing an axis for specialization of cortical systems. In particular, hemispheric specialization is a central organizing principle of the human brain that is hypothesized to contribute to fast, efficient processing of information in one hemisphere while minimizing the dependence on the other hemisphere. Cross-hemispheric information transfer occurs by way of the anterior and posterior commissures, and the corpus callosum. Most fibers in human corpus callosum are under 2 μm in diameter. Cross-hemispheric conduction delays have likely exerted an escalating constraint on cortical organization as hominin brain size expanded. The human cerebral cortex is triple the size of modern great apes and has about 10 times larger surface area than the macaque monkey. Given that cross-hemispheric axonal distances often exceed 100 mm in the human brain, interaction between the hemispheres is slow. For example, a one-way cross-hemispheric is estimated to take from 10 to 25 ms depending on fiber diameter. Temporal constraints are mitigated if local circuits within a hemisphere become specialized for processing tasks such that they minimize interaction with the other hemisphere.

Hemispheric asymmetry is most prominent in higher-order cognitive functions, particularly language, memory, and attention, while sensory and motor functions involve more symmetric areas between the hemispheres. This heterogeneity across functional systems is reflected by the anatomical arrangement in corpus callosum. Thick, highly myelinated, fast-conducting fibers preferentially locate in callosal regions connecting the primary and secondary sensorimotor areas, while thin, poorly myelinated fibers are densest in the genu and mid splenium, callosal regions that connect prefrontal and higher order association areas in parietal and temporal lobes. These anatomical characteristics suggest that the human brain may have evolved a connectional architecture biased to within-hemispheric processing in the higher-order association areas while preserving cross-hemispheric coordination for certain unimodal sensorimotor functions. Mapping this heterogeneous distribution of specialization across the cortex is challenging because specialization of multiple brain systems needs to be measured within the same individual. The difficulty in quantifying the specialization of multiple brain systems may also contribute to the controversy over the potential relation between various specialized functions. For example, early models have posited a single causal factor controlling the lateralization of multiple systems, whereas recent evidence suggests functional laterality of different systems might be driven by separable factors.

A further open question about hemispheric specialization is related to how distinct processing domains are controlled. Recent studies suggest that, depending on the task domain, the frontoparietal control network (FPN) might flexibly couple with either the default network or the dorsal attention network, two antagonistic systems subserving internally and externally directed cognition. To minimize lengthy inter-hemispheric transfer, one possible arrangement might be for networks involved in cognitive control to become functionally specialized between the two hemispheres. This hypothesis leads to a counterintuitive prediction that the control network might have functionally dissociable left-lateralized and right-lateralized portions, each contributing to a different set of lateralized functions through preferential interactions with distinct networks.

Determining the lateralization of brain functions is not only necessary for surgical planning but also important in brain development and psychiatric investigations. Traditionally, the lateralization of brain function is investigated through study of lateralized brain lesions, split-brain patients, sodium amytal injection, intraoperative brain stimulation, and/or task-based neuroimaging. More recently, functional lateralization has been estimated during rest by contrasting the intrinsic functional connectivity in two hemispheres. However, technical challenges faced by these approaches stem from their reliance on identifying homotopic regions in two hemispheres, which are inevitably confounded by anatomical asymmetry of the human brain. Anatomical asymmetry may span across multiple scales, from overall morphology, cortical folding pattern surface area and gray matter thickness, to microscopically measured cyto-architecture and the organization of micro-circuitry.

Therefore, given the above, there is a need for systems and methods for reliable measurement of brain functional lateralization without confounding factors included in previous approaches.

SUMMARY

The present invention overcomes the aforementioned drawbacks by providing a system and method directed to measuring a functional specialization of a subject brain using functional magnetic resonance imaging (fMRI) data. Specifically, the present invention provides an approach for determining a specialization profile for regions of interest in the brain of a subject using a measure that does not necessitate direct contrast between homotopic regions, but relies instead on relative composition between within- and cross-hemisphere functional connectivity across brain regions.

In accordance with one aspect of the disclosure, a method for measuring a functional specialization of a subject brain is provided. The method includes providing a set of functional magnetic resonance imaging (fMRI) data acquired during a resting state of a subject, and selecting a plurality of seed voxels associated with locations in hemispheres of a brain of the subject. The method also includes determining a degree of within-hemisphere connectivity for each seed voxel using the fMRI data, determining a degree of cross-hemisphere connectivity for each seed voxel using the fMRI data, and computing an autonomy index for each seed voxel using the degree of within-hemisphere connectivity and the degree of cross-hemisphere connectivity, wherein the autonomy index is indicative of a connectivity asymmetry between the hemispheres. The method further includes generating a report indicative of a specialization profile determined for a region of interest in the brain of the subject.

In accordance with an other aspect of the disclosure, a system for measuring a functional specialization of a subject brain is provided. The system includes an input configured to receive a set of functional magnetic resonance imaging (fMRI) data acquired during a resting state of a subject, and at least one processor configured to select a plurality of seed voxels associated with locations in hemispheres of a brain of the subject, determine a degree of within-hemisphere connectivity for each seed voxel using the fMRI data, and determine a degree of cross-hemisphere connectivity for each seed voxel using the fMRI data. The at least one processor is also configured to compute an autonomy index for each seed voxel using the degree of within-hemisphere connectivity and the degree of cross-hemisphere connectivity, wherein the autonomy index is indicative of a connectivity asymmetry between the hemispheres, and generate a report indicative of a specialization profile determined for a region of interest in the brain of the subject. The system also includes an output configured to display the report.

The foregoing and other advantages of the invention will appear from the following description.

BRIEF DESCRIPTION OF THE DRAWINGS

FIGS. 5A, 5B and 5C are graphical examples illustrating that hemispheric specialization during rest is predictive of language lateralization during task.

DETAILED DESCRIPTION

Figure 1:
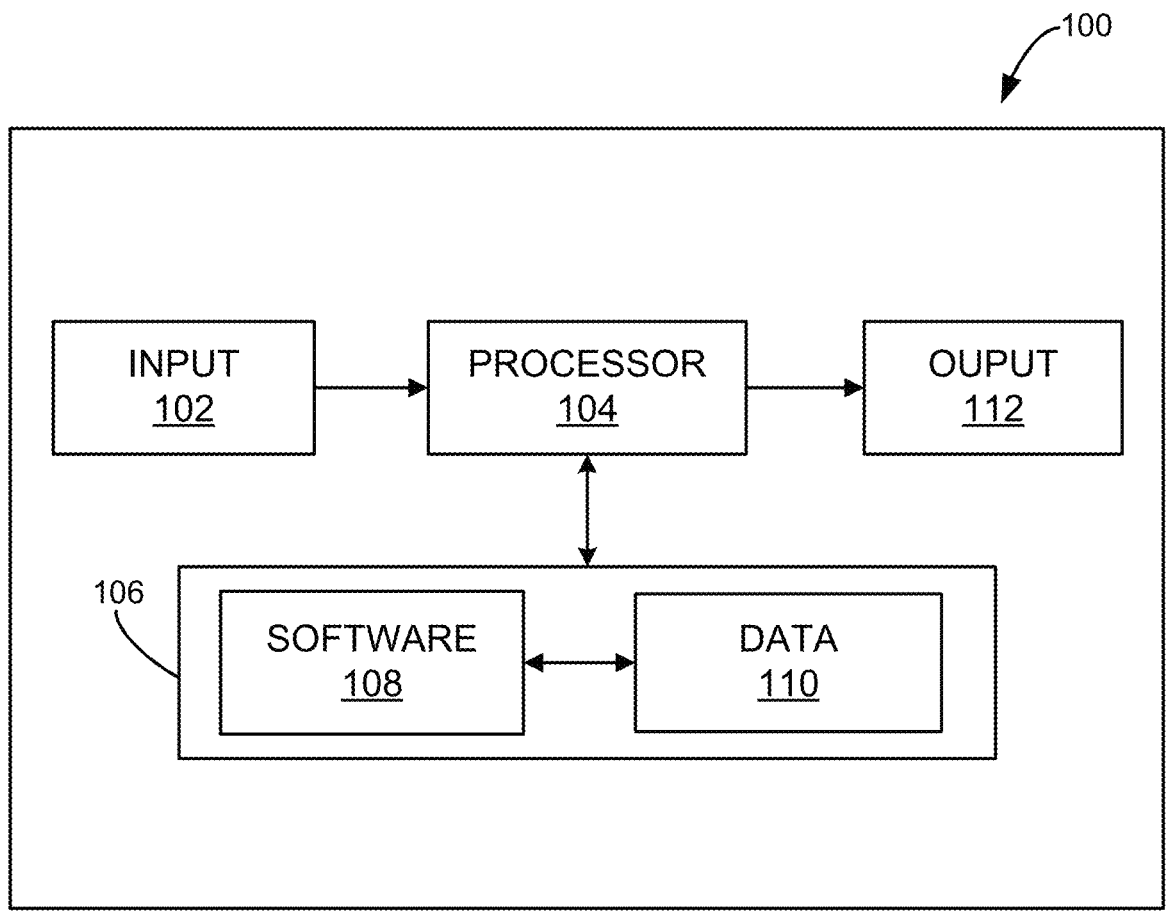
FIG. 1 is a schematic of an example system for measuring functional specialization of the brain of a subject.

Turning to FIG. 1, a block diagram is shown of an example of a system 100 configured for measuring functional brain specialization for a subject. The system 100 generally may include an input 102, at least one processor 104, a memory 106, an output 108, and any device for reading computer-readable media (not shown). The system 100 may be, for example, a workstation, a notebook computer, a personal digital assistant (PDA), a multimedia device, a network server, a mainframe or any other general-purpose or application-specific computing device. The system 100 may operate autonomously or semi-autonomously, or may read executable software instructions from a computer-readable medium (such as a hard drive, a CD-ROM, flash memory and the like), or may receive instructions from a user, or any another source logically connected to computer or device, such as another networked computer or server, via the input 102.

The input 102 may take any shape or form, as desired, for operation of the system 100, including the ability for selecting, entering or otherwise specifying parameters consistent with operating the system 100. In some aspects, the input 102 may be configured to receive functional magnetic resonance image (fMRI) data, associated with resting states, task states, and any other states of consciousness of a subject(s). Such data may be pre-processed, filtered and corrected using known methods and technologies.

Among the processing tasks for operating the system 100, the at least one processor 104 may also be configured to receive raw or processed fMRI data, among other data. In some configurations, or the at least one processor 104 may also be configured to carry out any number of post-processing steps on the fMRI data, including manipulating, filtering, enhancing, or correcting the fMRI data in relation to artifacts, and errors, due to scanner characteristics, subject motion, physiological sources, and so forth. In addition, the at least one processor 104 may be capable of performing computations using signals derived from raw or processed fMRI data. For example, the at least one processor 104 may be capable of generating time-series signals consistent with locations, or voxels, in regions of interest within the brain of a subject, such as functional networks. The at least one processor 104 may also be capable of selecting any number of seed voxels and performing a correlation process to generate a number of correlation values, using time-series signals corresponding to locations within or between such regions of interest. Additionally, the at least one processor 104 may also be configured to determine a specialization profile, or brain functional lateralization, of regions of interest, such as functional networks, in the brain of a subject. Specifically, this may involve computations directed to autonomy, specialization, indices or metrics, and any combinations thereof, that make use of the generated correlation values to determine an imbalance, or asymmetry, between within-hemisphere and cross-hemisphere connectivity.

The memory 106 may contain software 110 and data 112, and may be configured for storage and retrieval of processed information and data to be processed by the processor 104. In some aspects, the software 110 may contain instructions directed to estimating a specialization profile, as mentioned. The data 112 may take include any data necessary for operating the system 100, and may include any raw or processed information in relation to time-series fMRI data, and subject map(s).

In addition, the output 108 may take any suitable shape or form, as desired, and may be configured for displaying, in addition to other desired information, any information in relation to a specialization of a region of interest, such as a functional network, in the brain of a subject. For example, the output 108 may be configured to display any indices, metrics, or maps, or any combinations thereof, indicative of specialization, or lateralization of any regions of interest in the brain of a subject.

Figure 2:
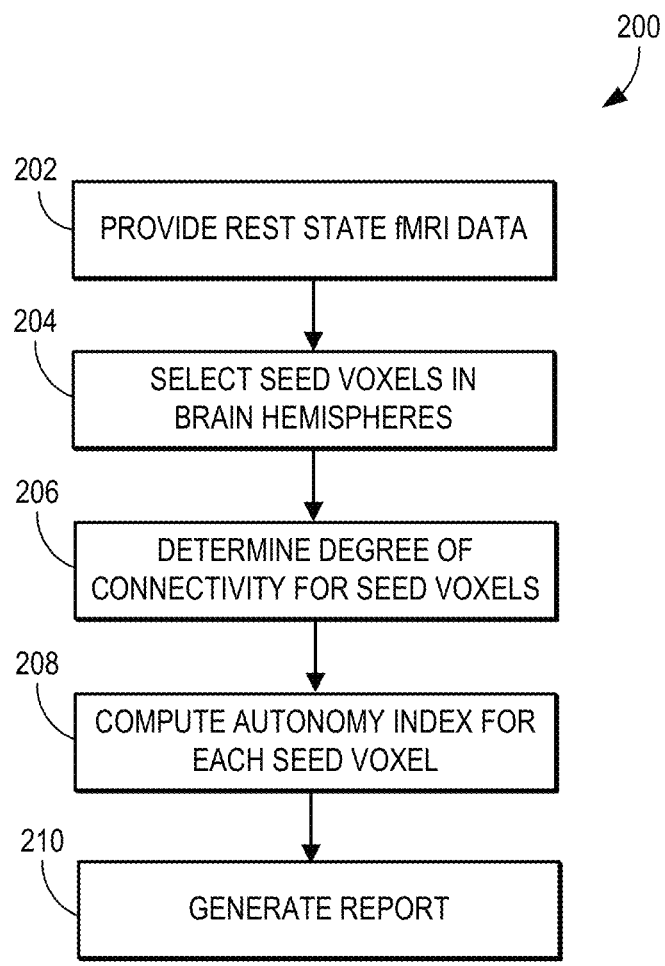
FIG. 2 is a flowchart setting forth steps for a method of measuring functional specialization of the brain of a subject using functional magnetic resonance imaging ("fMRI") data.

Turning to FIG. 2, a flowchart is shown, illustrating an example of a process 200 for estimating lateralization, specialization, or both, of brain function of a subject, in accordance with some embodiments the present invention. The process begins at process block 202 where resting-state fMRI data is provided. In some aspects, the fMRI data may be acquired at process block 202 using a magnetic resonance system ("MRI"), as will be described. Then, at process block 204, a plurality of seed voxels associated with locations in the hemispheres of the subject's brain are selected.

At process block 206, a degree of within-hemisphere connectivity and a degree of cross-hemisphere connectivity is determined for each seed voxel. These degrees of connectivity are determined using time-series signals derived from the provided fMRI data.

As an example, the degree of within-hemisphere connectivity can be determined by first correlating time-signals associated with a seed voxel with time-signals corresponding to other locations, or voxels, located in the ipsilateral hemisphere, which is the same hemisphere as the particular seed voxel. Using correlation values computed in this manner, the number of correlated ipsilateral voxels is identified. In some aspects, it may be advantageous to utilize only strongly correlated voxels; thus, a threshold correlation value may be selected and only those correlation values that are above the threshold can be used in those instances. In some embodiments, the degree of within-hemisphere connectivity can be normalized by normalizing the number of correlated ipsilateral voxels with the total number of voxels in the ipsilateral hemisphere.

As an example, the degree of cross-hemisphere connectivity can be determined using the number of correlated contralateral voxels identified. In some embodiments, the degree of cross-hemisphere connectivity can be normalized by the total number of voxels in the contralateral hemisphere.

At process block 208, a metric that defines an asymmetry between the right and left hemispheres of the subject's brain, may by calculated for each seed voxel. As an example, the metric can be referred to as an autonomy index that is computed by taking the difference between the degree of within-hemisphere connectivity and the degree of cross-hemisphere connectivity according to:

$$AI = N_i/V_i - N_c/V_c \qquad (1);$$

where $N_i$, $N_c$ are the numbers of strongly correlated voxels, as described, in the ipsilateral or contralateral hemisphere, respectively, and $V_i$, $V_c$ are the total number of voxels in the ipsilateral or the contralateral hemisphere, respectively. Thus, in some aspects, to estimate a specialization of specific region-of-interest (ROI), such as a functional network, in the brain of a subject, AI values for seed voxels located within the boundary of the ROI may be combined. For example, a mean or average autonomy index may be computed for an ROI. As an example, the ROI may correspond to a particular functional network, such as the frontoparietal network.

Finally, at process block 210 a report is generated. The report may take any suitable shape or form as desired. For example, a generated report may be in the form of two or three-dimensional maps, indicative of a specialization profile, or hemisphere lateralization, of functional connectivity networks in relation to anatomical features, portions or perspectives of the brain of the subject.

Figure 3:
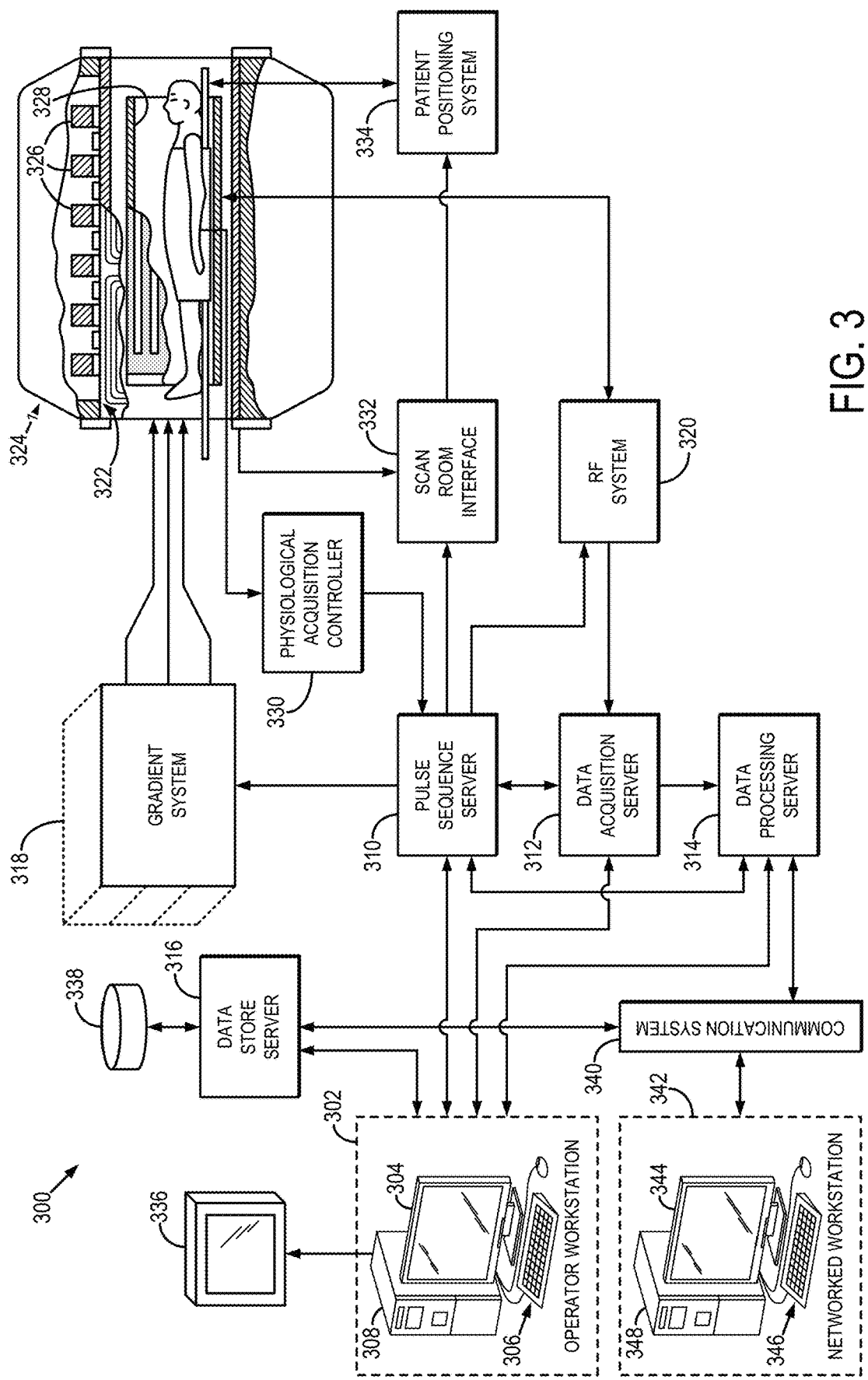
FIG. 3 is a block diagram of an example of a MRI system.

Referring particularly now to FIG. 3, an example of a MRI system 300 is illustrated, for use in accordance with the present invention. The MRI system 300 includes an operator workstation 302, which will typically include a display 304; one or more input devices 306, such as a keyboard and mouse; and a processor 308. The processor 308 may include a commercially available programmable machine running a commercially available operating system. The operator workstation 302 provides the operator interface that enables scan prescriptions to be entered into the MRI system 300. In general, the operator workstation 302 may be coupled to four servers: a pulse sequence server 310; a data acquisition server 312; a data processing server 314; and a data store server 316. The operator workstation 302 and each server 310, 312, 314, and 316 are connected to communicate with each other. For example, the servers 310, 312, 314, and 316 may be connected via a communication system 340, which may include any suitable network connection, whether wired, wireless, or a combination of both. As an example, the communication system 340 may include both proprietary or dedicated networks, as well as open networks, such as the internet.

The pulse sequence server 310 functions in response to instructions downloaded from the operator workstation 302 to operate a gradient system 318 and a radiofrequency ("RF") system 320. Gradient waveforms necessary to perform the prescribed scan are produced and applied to the gradient system 318, which excites gradient coils in an assembly 322 to produce the magnetic field gradients $G_x$, $G_y$, and $G_z$, used for position encoding magnetic resonance signals. The gradient coil assembly 322 forms part of a magnet assembly 324 that includes a polarizing magnet 326 and a whole-body RF coil 328.

RF waveforms are applied by the RF system 320 to the RF coil 328, or a separate local coil (not shown in FIG. 3), in order to perform the prescribed magnetic resonance pulse sequence. Responsive magnetic resonance signals detected by the RF coil 328, or a separate local coil (not shown in FIG. 3), are received by the RF system 320, where they are amplified, demodulated, filtered, and digitized under direction of commands produced by the pulse sequence server 310. The RF system 320 includes an RF transmitter for producing a wide variety of RF pulses used in MRI pulse sequences. The RF transmitter is responsive to the scan prescription and direction from the pulse sequence server 310 to produce RF pulses of the desired frequency, phase, and pulse amplitude waveform. The generated RF pulses may be applied to the whole-body RF coil 328 or to one or more local coils or coil arrays (not shown in FIG. 3).

The RF system 320 also includes one or more RF receiver channels. Each RF receiver channel includes an RF preamplifier that amplifies the magnetic resonance signal received by the coil 328 to which it is connected, and a detector that detects and digitizes the I, and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2} \qquad (2);$$

and the phase of the received magnetic resonance signal may also be determined according to the following relationship:

$$\varphi = \tan^{-1}\left(\frac{Q}{I}\right). \qquad (3)$$

The pulse sequence server 310 also optionally receives patient data from a physiological acquisition controller 330. By way of example, the physiological acquisition controller 330 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 310 to synchronize, or "gate," the performance of the scan with the subject's heart beat or respiration.

The pulse sequence server 310 also connects to a scan room interface circuit 332 that receives signals from various sensors associated with the condition of the patient and the magnet system. It is also through the scan room interface circuit 332 that a patient positioning system 334 receives commands to move the patient to desired positions during the scan.

The digitized magnetic resonance signal samples produced by the RF system 320 are received by the data acquisition server 312. The data acquisition server 312 operates in response to instructions downloaded from the operator workstation 302 to receive the real-time magnetic resonance data and provide buffer storage, such that no data is lost by data overrun. In some scans, the data acquisition server 312 does little more than pass the acquired magnetic resonance data to the data processor server 314. However, in scans that require information derived from acquired magnetic resonance data to control the further performance of the scan, the data acquisition server 312 is programmed to produce such information and convey it to the pulse sequence server 310. For example, during prescans, magnetic resonance data is acquired and used to calibrate the pulse sequence performed by the pulse sequence server 310. As another example, navigator signals may be acquired and used to adjust the operating parameters of the RF system 320 or the gradient system 318, or to control the view order in which k-space is sampled. In still another example, the data acquisition server 312 may also be employed to process magnetic resonance signals used to detect the arrival of a contrast agent in a magnetic resonance angiography ("MRA") scan. By way of example, the data acquisition server 312 acquires magnetic resonance data and processes it in real-time to produce information that is used to control the scan.

The data processing server 314 receives magnetic resonance data from the data acquisition server 312 and processes it in accordance with instructions downloaded from the operator workstation 302. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 314 are conveyed back to the operator workstation 302 where they are stored. Real-time images are stored in a data base memory cache (not shown in FIG. 3), from which they may be output to operator display 312 or a display 336 that is located near the magnet assembly 324 for use by attending physicians. Batch mode images or selected real time images are stored in a host database on disc storage 338. When such images have been reconstructed and transferred to storage, the data processing server 314 notifies the data store server 316 on the operator workstation 302. The operator workstation 302 may be used by an operator to archive the images, produce films, or send the images via a network to other facilities.

The MRI system 300 may also include one or more networked workstations 342. By way of example, a networked workstation 342 may include a display 344; one or more input devices 346, such as a keyboard and mouse; and a processor 348. The networked workstation 342 may be located within the same facility as the operator workstation 302, or in a different facility, such as a different healthcare institution or clinic.

The networked workstation 342, whether within the same facility or in a different facility as the operator workstation 302, may gain remote access to the data processing server 314 or data store server 316 via the communication system 340. Accordingly, multiple networked workstations 342 may have access to the data processing server 314 and the data store server 316. In this manner, magnetic resonance data, reconstructed images, or other data may exchanged between the data processing server 314 or the data store server 316 and the networked workstations 342, such that the data or images may be remotely processed by a networked workstation 342. This data may be exchanged in any suitable format, such as in accordance with the transmission control protocol ("TCP"), the internet protocol ("IP"), or other known or suitable protocols.

The above-described systems and methods may be further understood by way of example. The examples offered herein are for illustrative purposes only, and are not intended to limit the scope of the invention in any way. Indeed, various modifications of the invention in addition to those shown and described herein will become apparent to those skilled in the art from the foregoing description and the following example falls within the scope of the appended claims. For example, data in relation to specific regions of interest or functional networks are presented, although it may be understood that analyzing other regions may be possible, and still considered to be within the scope of the present invention.

Example I

The present study revealed that hemispheric specialization has a nonuniform distribution across the cerebral cortex. Specialization is strongest in the heteromodal association regions that are estimated to preferentially depend on relatively small callosal fibers and are also characterized by preferential long-range functional connectivity. Pathways for associative processing are critical for achieving behavioral flexibility but require integration among brain regions that are far apart. Given that crosshemispheric transfer incurs extra processing costs, specialization of these circuits may bring advantages for time-critical tasks. By contrast, unimodal systems in each hemisphere include local, modular processing circuits often connected to midline or mirrored body representations that necessarily require interaction between the two hemispheres.

Methods

Participants

Two datasets with a total of 1006 young healthy participants were employed in the present study. The first dataset included 1,000 individuals that each performed one or two resting-state fMRI runs during an eyes open resting condition. The 1,000 subjects were divided into two independent sub-samples that were matched for age, sex and MRI scanner (n=500 for each; labeled as the Discovery and Replication samples). The second dataset were acquired from 55 subjects (49 subjects were included in the first dataset) who performed a semantic classification task.

Resting-State fMRI Data Acquisition and Preprocessing

Resting-state fMRI data were collected on matched 3T Tim Trio scanners (Siemens, Erlangen, Germany) using a 12-channel phased-array head coil. Images were acquired using a gradient-echo echo-planar pulse sequence sensitive to blood oxygenation level-dependent (BOLD) contrast (TR=3000 ms, TE=30 ms, flip angle=85°, 3 mm×3 mm×3 mm voxels, FOV=216 and 47 slices collected with interleaved acquisition with no gap between slices). Whole brain coverage included the entire cerebellum. Subjects were instructed to stay awake, keep their eyes open, and minimize head movement; no other task instruction was provided.

Resting-state fMRI data were processed using the FreeSurfer version 4.5.0 software package, an open source software suite for processing and analyzing brain MRI images. The structural and functional images were aligned using boundary-based registration within the FsFast software package. The resting-state BOLD fMRI data were then aligned to a common spherical coordinate system via sampling from the middle of the cortical ribbon in a single interpolation step.

Hemispheric Autonomy Index

A uniform sub-sampling was performed for the cerebrum (voxel size 8 mm×8 mm×8 mm) and cerebellum (voxel size 6 mm×6 mm×6 mm) in the FreeSurfer nonlinear volumetric space, resulting in 1455 voxels in the left hemisphere and 1479 voxels in the right hemisphere of cerebrum, as well as 525 voxels in left hemisphere and 524 voxels in the right hemisphere of cerebellum. As described, for each seed voxel, the degree of within-hemisphere connectivity and cross-hemisphere connectivity was computed by summing up the number of strongly correlated voxels (r>0.1) in the ipsilateral hemisphere and contralateral hemisphere of the seed, respectively. Each degree of connectivity was then normalized by the total number of voxels in the corresponding hemisphere. AI was then calculated as the difference between the normalized within-hemisphere connectivity and the normalized cross-hemisphere connectivity, according to Eqn. 1. AI was then determined for each voxel in the brain. Also, to estimate the specialization of specific functional networks, AI was averaged within the boundary of each functional network.

Estimating Language Lateralization

Fifty-five subjects each performed three task-based fMRI runs of an abstract/concrete semantic classification task. The task design manipulated familiarity to isolate regions specifically involved in controlled semantic retrieval. During a pre-scan familiarization phase, subjects repeatedly classified the same 4 words (2 abstract and 2 concrete) for 5 repetitions. During the scan, each run consisted of four 30-s "novel" blocks of task, four 30-s "familiar" blocks, and four 30-s block of fixation. In each novel block, 10 novel words (5 concrete and 5 abstract words in random order) were presented for 2-s with 1-s inter-stimulus interval. In the familiar block, the 4 practiced words were presented repeatedly. The subject's task was to indicate if each word was concrete or abstract independent of novelty. In total, 120 novel words and 4 familiar words were employed. Participants were instructed to respond by pressing a single key with the index finger of each hand. The MRI data acquisition parameters were identical to the resting state scan described above, except that 124 time points were acquired in each task run. Data were first analyzed using the general linear model in participants' native fMRI space. Brain regions participating in controlled semantic retrieval were isolated by contrasting the novel versus familiar condition. Similar to a previous approach, a language laterality index was calculated for each individual subject based on the asymmetric activations in two hemispheres.

Correlation to Evolutionary Cortical Expansion and Long-Distance Connectivity

The map of regional evolutionary cortical expansion between an adult macaque and the average human adult PALS-B12 atlas was provided by colleagues. This map only included data in right hemisphere. For each brain voxel, the degree of long-distance connectivity (r>0.25) was computed outside a neighborhood of 25 mm and the degree of local connectivity (r>0.25) was computed within a neighborhood of 12 mm. The percentage of long-distance connectivity was then computed for each voxel. To produce FIG. 8, data in the right hemisphere were projected to the Conte69 164k_fs_LR mesh. The data were extracted using the Caret Surface Statistics Toolbox for the correlation analysis. The absolute expansion ratio was normalized by taking the logarithm and subtracted with a constant.

Testing the Potential Impact of Spatial Dependence on Correlation Analyses.

To test the potential impact of spatial dependence between neighboring vertices on correlation analysis, a repeated (n=1000) random sampling of 7% of the vertices was performed, and the correlation coefficient on the subsets of the vertices was computed. For each subset, the Durbin-Watson test was performed to estimate the spatial dependence (DW>2). Correlation coefficients were averaged across the 1000 iterations.

Results

Prominent Hemispheric Specialization of Association Cortices

Figure 4:
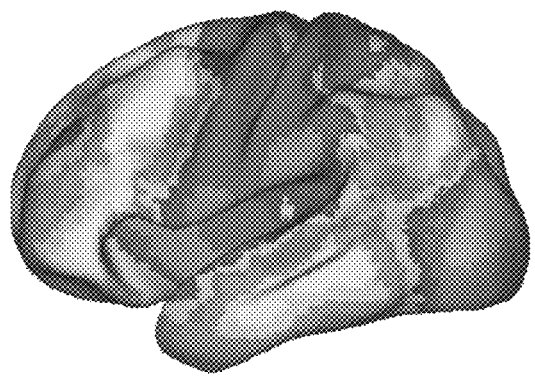
FIG. 4 is a graphical illustration of hemispheric specialization for two subject groups.
Figure 4:
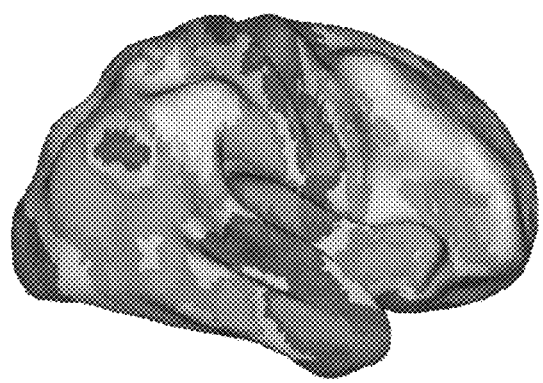
Figure 4:
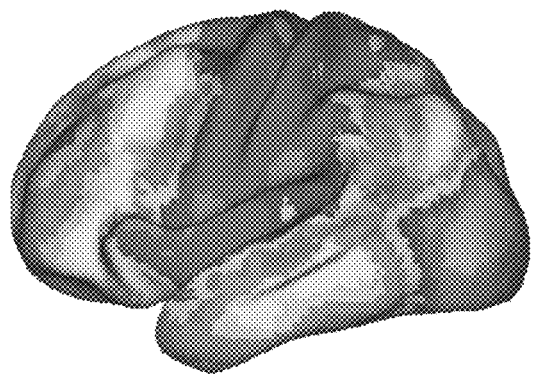
Figure 4:
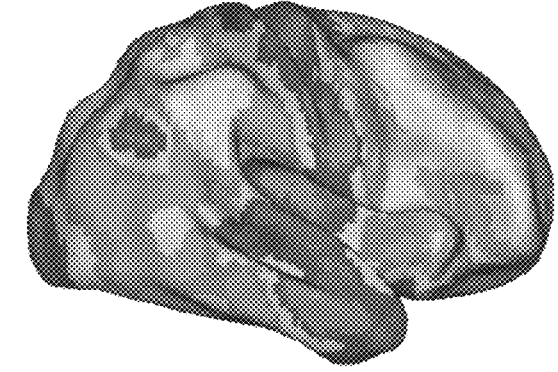
Figure 4:

To quantify functional specialization of the human brain, AI was computed at each brain voxel in the Discovery sample (N=500) and then replicated in the independent Replication sample (N=500). Strong hemispheric specialization was observed in the association cortices including the lateral prefrontal, inferior parietal and temporal regions (FIG. 4). Visual, somatosensory and motor cortices exhibited minimal autonomy. It is noteworthy that hemispheric specialization in the two hemispheres demonstrated different patterns. In the left hemisphere, strong specialization was observed in inferior prefrontal and temporal regions overlapping the default network and regions traditionally associated with language. In the right hemisphere, strong specialization was observed in the insula, angular gyrus and supramarginal gyrus that overlap with regions involved in attention. A third pattern was also noted, namely portions of the prefrontal cortex and inferior parietal lobule that overlap with regions implicated in cognitive control (e.g., the FPN) showed strong specialization in both hemispheres.

Hemispheric Specialization Estimated During Rest Predicts Language Lateralization During Task To explore the relation between hemispheric specialization estimated by AI and traditional task-based estimates of lateralization, task data from 55 subjects was examined. Each subject performed three fMRI runs involving semantic classification of words. The task design manipulated familiarity to isolate regions specifically involved in controlled semantic retrieval). Task-based language lateralization was calculated for each subject according to a previous approach. Also, AI was averaged for each subject within a mask of the most specialized regions derived from the 1,000 subjects (FIG. 5a). A significant correlation (r=0.52, p<0.001) was found between left hemisphere AI and the language lateralization index (FIG. 5c), indicating a modest relation between intrinsic hemispheric specialization and language lateralization. The individuals with the lowest left hemisphere AI values all demonstrated a typical bilateral or flipped language lateralization during the language task.

These a typical lateralization patterns were manifested both in the cerebral cortex and the cerebellum.

Frontoparietal Control Network is Specialized in Both Hemispheres

Using the estimates of hemispheric autonomy, the relative specialization of networks spread across the full cerebral cortex was assessed. For this analysis, the cerebral cortex was first parcellated into 7 functional networks using a clustering approach, including the FPN, ventral and dorsal attention, default limbic, sensorimotor and visual networks. Specialization of a network was then estimated by averaging AI values within the boundary of the network in each hemisphere.

Figures 6A, 6B:
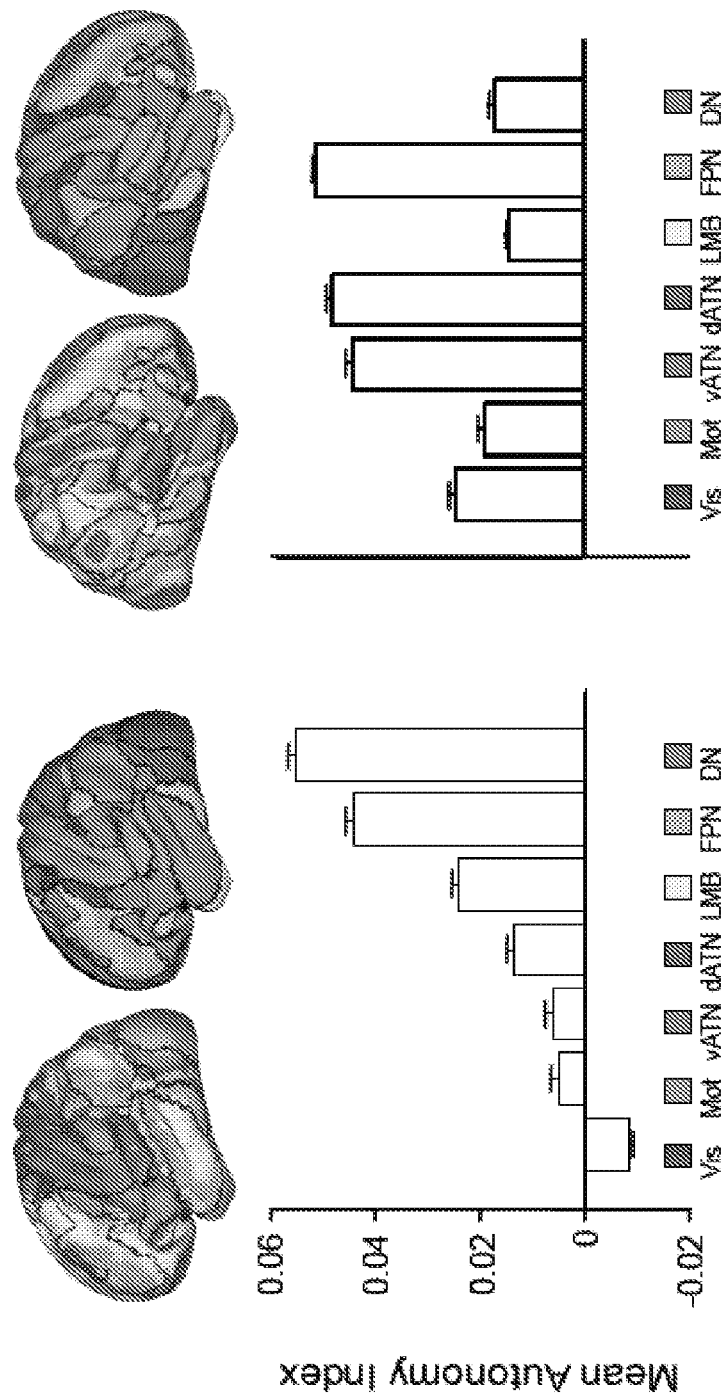
FIGS. 6A and 6B are graphical examples illustrating that the frontoparietal control network (FPN) is specialized in both hemispheres.

The degree of specialization differed across functional networks. A ranking of the networks according to AI indicated that the default network and FPN were among the most specialized in the left hemisphere while visual and sensorimotor networks were least specialized (FIG. 6a). Functional specialization in the right hemisphere exhibited a different pattern. While the FPN was again among the most specialized networks, the ventral attention and dorsal attention networks demonstrated particularly strong specialization in the right hemisphere (FIG. 6b). The heterogeneity of specialization across networks was supported by the significant difference between any two networks (two tailed t-test, $p<10^{-8}$ for all comparisons except that $p<10^{-4}$ for the comparison between dorsal attention and ventral attention in the right hemisphere). The ranking of specialization across the functional networks could be independently estimated in the cerebellum, where the AI showed a highly similar ranking pattern but in the contralateral hemisphere, suggesting the distribution was unlikely due to technical confounds including misalignment.

Figure 7:
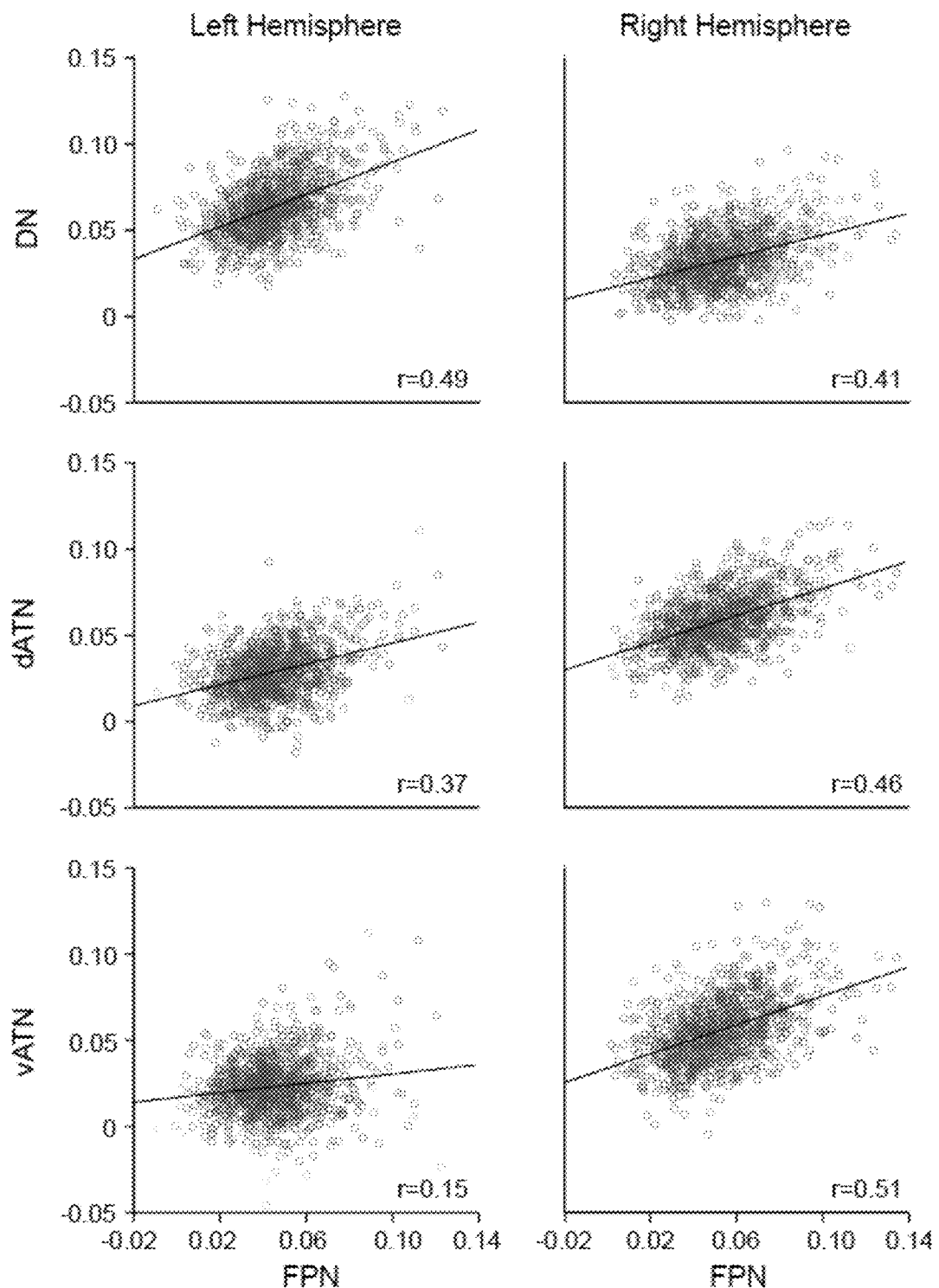
FIG. 7 is a graphical example illustrating that specialization of the frontoparietal control network tracks distinct networks in both hemispheres.

Specialization of the Frontoparietal Control Network Tracks Distinct Networks in the Two Hemispheres To investigate the relation between the specialization of the FPN, which was specialized in both hemispheres, and other networks, AI values for each of the 7 networks were correlated across the 1,000 subjects (FIG. 7). The idea behind this analysis is that individual differences in network coupling strength might provide information about how the distinct networks are interacting. In the left hemisphere, the strongest correlation was found between the AI of the FPN and the default network (r=0.49), while AI of the FPN and attention networks (dorsal attention and ventral attention) showed weaker correlation (ANCOVA, $p<10^{-5}$ and $p<10^{-16}$, respectively, r=0.37 with the dorsal attention and r=0.15 with the ventral attention networks). However, in the right hemisphere, the AI revealed the strongest correlation between the FPN and both attention networks (r=0.51 with the ventral attention and r=0.46 with the dorsal attention networks) but a weaker correlation with the default network (ANCOVA, $p<0.005$ and $p<0.001$, respectively. r=0.41 with the default network). These correlation patterns support the hypothesis that specialization of the FPN is more strongly coupled with the default network in the left hemisphere and strongly coupled with attention networks in right hemisphere. The different coupling strength among networks could be independently replicated in the cerebellum. In the right cerebellar hemisphere, AI of the FPN was more strongly correlated with that of the default regions than the ventral and dorsal attention regions (ANCOVA, $p<10^{-10}$ and $p<10^{-10}$, respectively). In the left cerebellar hemisphere, AI of the FPN was more strongly coupled with the attention regions than the default regions (ANCOVA, $p<10^{-4}$ and $p<0.05$, respectively).

To explore the possibility that the observed correlation patterns were confounded by the anatomical adjacency among networks, the network boundaries were eroded by 6 mm thus a set of core regions were derived for the FPN, default and attention networks. The correlation analyses were then repeated based on these core regions, which were well separated from each other. The correlation patterns in left hemisphere and right hemisphere preserved, namely AI in the FPN was more strongly coupled with the default network than attention networks (ANCOVA, $p<0.001$ and $p<10^{-7}$, respectively) in the left hemisphere, but more strongly coupled with the attention networks than the default network (ANCOVA, $p<0.0005$ and $p<0.0005$, respectively) in the right hemisphere. While this analysis cannot rule out the possibility of asymmetric spatial correlation contributing to our observations, it suggests that a confounding effect, if present, is subtle and not a simple product of spatial adjacencies of the networks.

Figure 8:
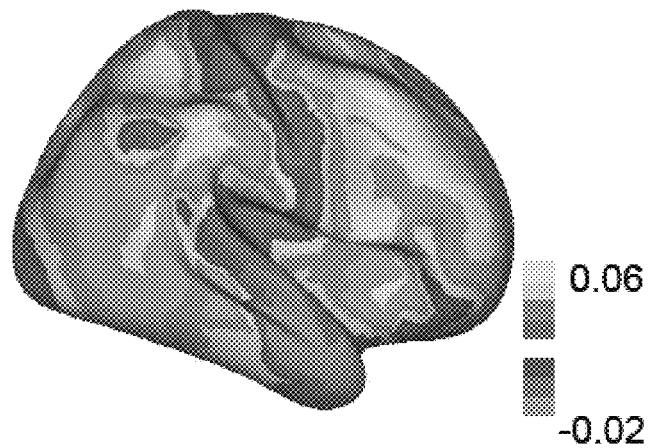
FIG. 8 is a graphical example illustrating a comparison of hemispheric specialization, evolutionary cortical expansion and distant connectivity.
Figure 8:
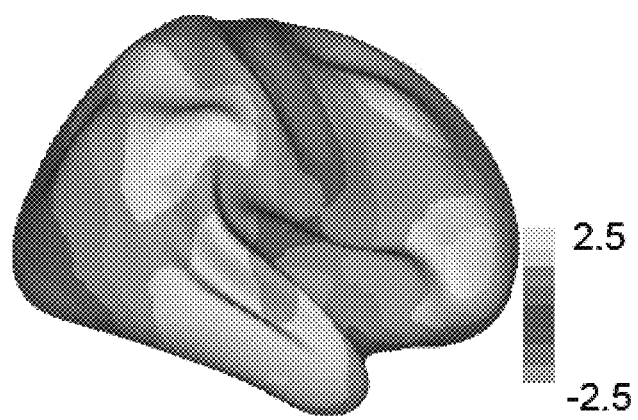
Figure 8:
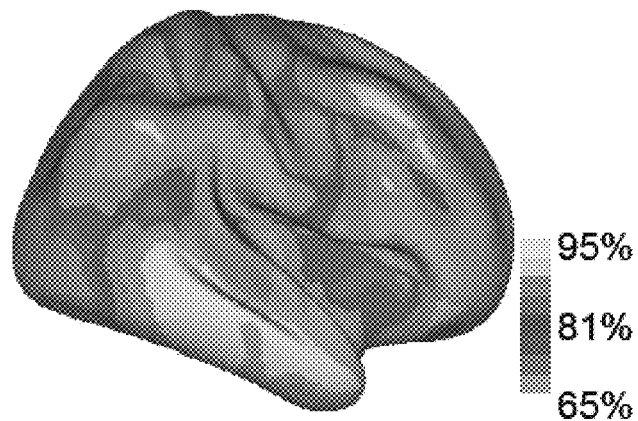

Hemispheric Specialization is Related to Long-Distance Connectivity and Evolutionary Cortical Expansion Hemispheric specialization may relate to human brain expansion. It was explored whether specialization measured by AI is correlated with regional evolutionary cortical expansion using estimates of cortical expansion derived from the comparison between macaques and humans. A moderate correlation (r=0.48, $p<0.0001$) between hemispheric specialization and evolutionary cortical expansion was observed (FIG. 8). The degree of local connectivity and long-distance connectivity was also quantified and the percentage of long-distance connectivity was computed at each voxel. A modest correlation (r=0.20, $p<0.0001$) was observed between hemispheric specialization and long-distance connectivity.

In summary, hemispheric specialization has long been a core research topic with important implications in understanding human brain evolution, development, and various neurological diseases. The present invention provides a system and method for measuring or quantifying a specialization profile across the full cerebral cortex of a subject using intrinsic functional MRI data. Specifically, based upon determined compositions of within- and cross-hemispheric connectivity, a hemispheric specialization may be measured using a novel metric that quantifies an asymmetry, or imbalance, between within- and cross-hemispheric interactions, in an approach that does not rely on assumptions regarding bilateral anatomic symmetries. Therefore, the approach of the present invention avoids confounding results due to homotopic region selection, as utilized by previous technologies.

Using data gathered from a large cohort, demonstrations were provided herein showing that hemispheric specialization may be capable of predicting language lateralization during a semantic retrieval task, which suggests that hemispheric specialization may be associated with traditional task-based asymmetry estimates. In addition, relations among hemispheric specialization, individual differences, and evolutionary cortical expansion were further explored. The gradient of specialization across different functional regions revealed that higher order association cortex exhibited the most prominent specialization while unimodal sensorimotor regions showed weaker specialization. Additionally, an intriguing finding demonstrated that the FPN included strong specialization in both hemispheres, but tracked distinct association networks in each hemisphere.

Use of the present invention, as described, may include applications in both investigative and clinical settings, such as pre-surgical planning and procedures. For example, the present invention may facilitate insight into the underpinnings of hemispheric specialization and reveal the potential relations among specialized functional networks. In addition, the approach of the present invention provides for functional lateralization of all brain regions to be quantified at once, including cerebral cortex, cerebellum and subcortical structures.

Features suitable for combinations and sub-combinations would be readily apparent to persons skilled in the art upon review of the present application as a whole. The subject matter described herein and in the recited claims intends to cover and embrace all suitable changes in technology.

The invention claimed is:

1. A method for measuring a functional specialization of a subject brain, the method comprising:
   i. providing a set of functional magnetic resonance imaging (fMRI) data representing a time-series of signals acquired from a brain of a subject during a resting state of the subject;
   ii. selecting a plurality of seed voxels associated with locations in a right hemisphere and a left hemisphere of a brain of the subject;
   iii. analyzing the time-series of signals represented in the fMRI data for each seed voxel against time-series signals outside of the seed voxel and located in an ipsilateral hemisphere of the brain to determine a degree of within-hemisphere connectivity for each seed voxel using the fMRI data;
   iv. analyzing the time-series of signals represented in the fMRI data for each seed voxel against time-series signals outside of the seed voxel and located in an contralateral hemisphere of the brain to determine a degree of cross-hemisphere connectivity for each seed voxel using the fMRI data;
   v. comparing the degree of degree of within-hemisphere connectivity for each seed voxel and the degree of cross-hemisphere connectivity for each seed voxel to a threshold correlation value to determine strongly correlated voxels in the ipsilateral or contralateral hemisphere;
   vi. computing an autonomy index for each seed voxel using the degree of within-hemisphere connectivity and the degree of cross-hemisphere connectivity, wherein the autonomy index is a measure of a connectivity asymmetry between the hemispheres created using a difference in a ratio of total number of voxels in the ipsilateral or the contralateral hemisphere and a ratio of strongly correlated voxels in the ipsilateral or contralateral hemisphere; and
   vii. displaying at least an image including a specialization profile determined based on computed autonomy indices for a region of interest in the brain of the subject.

2. The method of claim 1, wherein determining the degree of within-hemisphere connectivity includes normalizing a number of correlated ipsilateral voxels with a total number of voxels in an ipsilateral hemisphere.

3. The method of claim 1, wherein determining the degree of cross-hemisphere connectivity includes normalizing a number of correlated contralateral voxels with a total number of voxels in a contralateral hemisphere.

4. The method of claim 1, wherein the method further comprises determining the specialization profile by computing an average of computed autonomy indices for seed voxels located within the region of interest.

5. The method of claim 1, wherein the method further comprises determining a brain functional lateralization using the specialization profile.

6. A system for measuring a functional specialization of a subject brain, the system comprising:
   an input configured to receive a set of functional magnetic resonance imaging (fMRI) data representing a time-series of signals acquired from a brain of a subject during a resting state of the subject;
   at least one processor configured to:
   a. select a plurality of seed voxels associated with locations in hemispheres of a brain of the subject;
   b. analyze the time-series of signals represented in the fMRI data for each seed voxel against nine-series signals outside of the seed voxel and located in an ipsilateral hemisphere of the brain to determine a degree of within-hemisphere connectivity for each seed voxel using the fMRI data;
   c. analyze the time-series of signals represented in the fMRI data for each seed voxel against time-series si s outside of the seed voxel and located in an contralateral hemisphere of the brain to determine a degree of cross-hemisphere connectivity for each seed voxel using the fMRI data;
   d. compare the degree of within-hemisphere connectivity for each seed voxel and the degree of cross-hemisphere connectivity for each seed voxel to a threshold correlation value to determine strongly correlated voxels in the ipsilateral or contralateral hemisphere;
   e. compute an autonomy index for each seed voxel using the degree of within-hemisphere connectivity and the degree of cross-hemisphere connectivity, wherein the autonomy index is a measure of a connectivity asymmetry between the hemispheres crated using a difference in a ratio of total number of voxels in the ipsilateral or the contralateral hemisphere and a ratio of strongly correlated voxels in the ipsilateral or contralateral hemisphere;
   ef. generate a report including at least one image including a specialization profile determined for a region of interest in the brain of the subject; and
   a display configured to display the report including the at least one image.

7. The system of claim 6, wherein the at least one processor is further configured to determine the degree of within-hemisphere connectivity by normalizing a number of correlated ipsilateral voxels with a total number of voxels in an ipsilateral hemisphere.

8. The system of claim 6, wherein the at least one processor is further configured to determine the degree of cross-hemisphere connectivity by normalizing a number of correlated contralateral voxels with a total number of voxels in a contralateral hemisphere.

9. The system of claim 6, wherein the at least one processor is further configured to determine the specialization profile by computing an average of computed autonomy indices for seed voxels located within the region of interest.

10. The system of claim 6, wherein the at least one processor is further configured to determine a brain functional lateralization using the specialization profile.

* * * * *

UNITED STATES PATENT AND TRADEMARK OFFICE
CERTIFICATE OF CORRECTION

PATENT NO. : 11,412,975 B2
APPLICATION NO. : 14/672046
DATED : August 16, 2022
INVENTOR(S) : Hesheng Liu et al.

It is certified that error appears in the above-identified patent and that said Letters Patent is hereby corrected as shown below:

In the Specification

Column 10, Line 66, "a typical" should be --atypical--.

Column 11, Line 1, "a typical" should be --atypical--.

In the Claims

Column 14, Claim 6, Line 14, "nine-series" should be --time-series--.

Column 14, Claim 6, Lines 22-23, "si s" should be --signals--.

Column 14, Claim 6, Line 26, "the degree of" should be --the degree of degree of--.

Column 14, Claim 6, Line 38, "crated" should be --created--.

Column 14, Claim 6, Line 42, "ef." should be --f.--.

Signed and Sealed this
Seventh Day of February, 2023

Katherine Kelly Vidal
*Director of the United States Patent and Trademark Office*